United States Patent
Lin et al.

(10) Patent No.: US 10,153,441 B2
(45) Date of Patent: Dec. 11, 2018

(54) ORGANIC METAL COMPOUND, ORGANIC LIGHT-EMITTING DEVICE, AND LIGHTING DEVICE EMPLOYING THE SAME

(71) Applicant: INDUSTRIAL TECHNOLOGY RESEARCH INSTITUTE, Hsinchu (TW)

(72) Inventors: Jin-Sheng Lin, Taipei (TW); Jia-Lun Liou, Hengshan Township, Hsinchu County (TW); Meng-Hao Chang, New Taipei (TW); Han-Cheng Yeh, Taipei (TW); Mei-Rurng Tseng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 190 days.

(21) Appl. No.: 14/673,082

(22) Filed: Mar. 30, 2015

(65) Prior Publication Data
US 2016/0293861 A1    Oct. 6, 2016

(51) Int. Cl.
*H01L 51/00* (2006.01)
*C07F 15/00* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC .............. C07F 15/0033; C09K 11/06; C09K 2211/185; C09K 2211/1007;
(Continued)

(56) References Cited

U.S. PATENT DOCUMENTS

| | | | | |
|---|---|---|---|---|
| 5,484,922 A | * | 1/1996 | Moore | H05B 33/14 313/503 |
| 2002/0064681 A1 | * | 5/2002 | Takiguchi | C07F 15/0033 428/690 |

(Continued)

FOREIGN PATENT DOCUMENTS

| | | |
|---|---|---|
| CN | 102703059 A | 10/2012 |
| EP | 1 642 951 A2 | 4/2006 |

(Continued)

OTHER PUBLICATIONS

Deng et al., "Diphenylphosphorylpyridine-Functionalized Iridium Complexes for High-Efficiency Monochromic and White Organic Light-Emitting Diodes", J. Mater. Chem., vol. 22, Jun. 11, 2012, pp. 15910-15918.

(Continued)

*Primary Examiner* — Satya B Sastri
(74) *Attorney, Agent, or Firm* — Birch, Stewart, Kolasch & Birch, LLP

(57) ABSTRACT

Organic metal compounds, organic light-emitting devices, and lighting devices employing the same are provided. The organic metal compound has a chemical structure represented by formula (I):

(Continued)

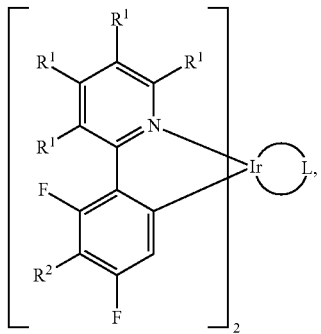

Formula (I)

wherein each $R^1$ is independent and can be hydrogen, halogen, $C_{1-10}$ alkyl group, $C_{5-10}$ cycloalkyl group, or $C_{5-12}$ aryl group; $R^2$ is trialkyl silyl group; and L is a picolinic acid ligand, a 2-(imidazol-2-yl) pyridine ligand, a 2-(4,5-dimethyl-imidazol-2-yl) pyridine ligand, a 3-(trifluoromethyl)-5-(pyridine-2-yl)-1,2,4-triazolate ligand, or a 3-(isobutyl)-5-(pyridine-2-yl)-1,2,4-triazolate ligand.

13 Claims, 3 Drawing Sheets

(51) Int. Cl.
 *C09K 11/06* (2006.01)
 *H05B 33/14* (2006.01)
(52) U.S. Cl.
 CPC ...... *H05B 33/14* (2013.01); *C09K 2211/1007* (2013.01); *C09K 2211/1014* (2013.01); *C09K 2211/1029* (2013.01); *C09K 2211/1044* (2013.01); *C09K 2211/1059* (2013.01); *C09K 2211/185* (2013.01); *H01L 51/0037* (2013.01); *H01L 2251/308* (2013.01)
(58) Field of Classification Search
 CPC .... C09K 2211/1029; C09K 2211/1044; C09K 2211/1059; C09K 2211/1096; H01L 51/0085
 See application file for complete search history.

(56) References Cited

U.S. PATENT DOCUMENTS

| | | |
|---|---|---|
| 2002/0182441 A1 | 12/2002 | Lamansky et al. |
| 2003/0072964 A1 | 4/2003 | Kwong et al. |
| 2004/0121184 A1* | 6/2004 | Thompson ............ C07F 15/004 428/690 |
| 2005/0156173 A1* | 7/2005 | Yamazaki ........... H01L 27/3244 257/72 |
| 2006/0228582 A1 | 10/2006 | Ragini et al. |
| 2008/0125591 A1 | 5/2008 | Chi et al. |
| 2011/0187265 A1 | 8/2011 | De Cola et al. |
| 2012/0169213 A1 | 7/2012 | De Cola et al. |
| 2012/0181511 A1 | 7/2012 | Ma et al. |
| 2013/0026452 A1 | 1/2013 | Kottas et al. |
| 2013/0049576 A1 | 2/2013 | Katakura et al. |
| 2013/0146848 A1 | 6/2013 | Ma et al. |

FOREIGN PATENT DOCUMENTS

| | | |
|---|---|---|
| EP | 2 182 002 A1 | 5/2010 |
| KR | 10-2013-0110934 A | 10/2013 |

OTHER PUBLICATIONS

Jung et al., "A Green Emitting Iridium (III) Complex with Narrow Emission Band and Its Application to Phosphorescence Organic Light-Emitting Diodes (OLEDs)", Organic Electronics, vol. 10, 2009, (published online May 27, 2009), pp. 1066-1073.

Kim et al., "Synthesis and Characterization of New Blue Light Emitting Iridium Complexes Containing a Trimethylsilyl Group", Journal of Materials Chemistry, Sep. 11, 2012, 6 pages.

Lee et al., "Improved Performance of Solution-Processable OLEDs by Silyl Substitution to Phosphorescent Iridium Complexes", Synthetic Metals, vol. 162, 2012, (available online Oct. 13, 2012), pp. 1961-1967.

Taiwanese Office Action dated Jan. 6, 2015 for Application No. 102147710.

Taiwanese Office Action dated Oct. 9, 2014 for Application No. 102147710.

Yeh et al., "New Dopant and Host Materials for Blue-Light-Emitting Phosphorescent Organic Electroluminescent Devices", Adv. Mater. vol. 17, No. 3, Feb. 10, 2005, pp. 285-289.

\* cited by examiner

ORGANIC METAL COMPOUND, ORGANIC LIGHT-EMITTING DEVICE, AND LIGHTING DEVICE EMPLOYING THE SAME

TECHNICAL FIELD

The disclosure relates to an organic metal compound, and an organic light-emitting device, and a lighting device employing the same.

BACKGROUND

An organic light-emitting diode (OLED) is a light-emitting diode employing an organic electroluminescent layer as an active layer. OLED display devices have high luminescent efficiency and long operating lifespans. In comparison with liquid-crystal displays, due to the characteristic of spontaneous emission, a device employing an organic light-emitting diode is free of a backlight source.

Generally, an organic light-emitting device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton, which results from the recombination of the hole and electron, can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of an OLED.

SUMMARY

According to an embodiment of the disclosure, the disclosure provides an organic metal compound having a Formula (I):

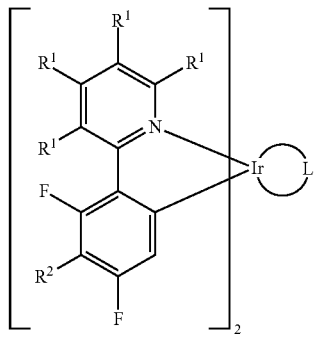

Formula (I)

wherein, each $R^1$ is independently an hydrogen, halogen, $C_{1-10}$ alkyl group, $C_{5-10}$ cycloalkyl group, or $C_{5-12}$ aromatic group; $R^2$ is trialkyl silyl group; and, L is picolinic acid ligand, 2-(imidazol-2-yl) pyridine ligand, 2-(4,5-dimethyl-imidazol-2-yl)pyridine ligand, 3-(trifluoromethyl)-5-(pyridine-2-yl)-1,2,4-triazolate ligand, or 3-(isobutyl)-5-(pyridine-2-yl)-1,2,4-triazolate ligand.

According to another embodiment of the disclosure, the disclosure provides an organic light-emitting device. In particular, the device includes a pair of electrodes; and a organic light-emitting element, disposed between the pair of electrodes, wherein the organic light-emitting element includes the aforementioned organic metal compound.

According to other embodiments of the disclosure, the disclosure also provides a lighting device including a lead frame; and the aforementioned organic light-emitting device, disposed on the lead frame.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
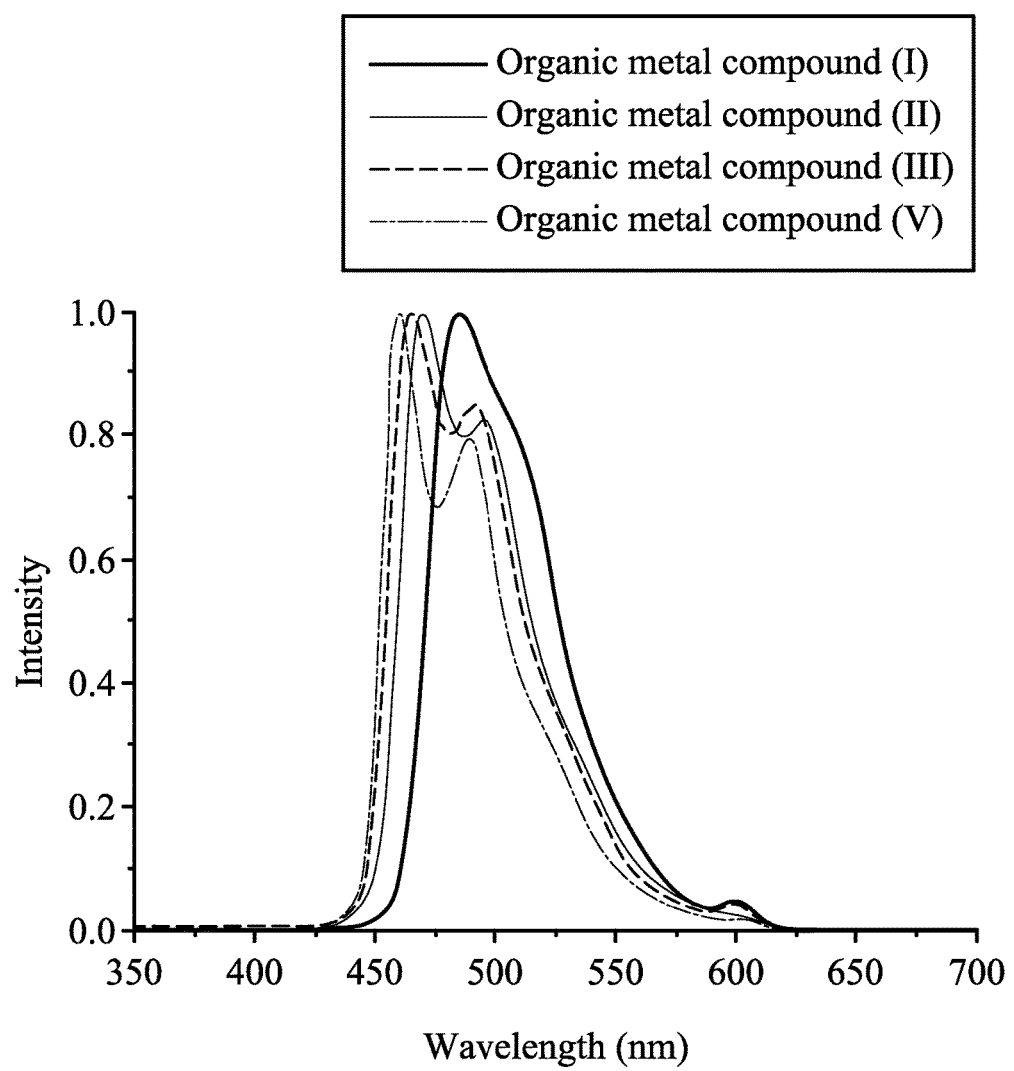
FIG. 1 shows photoluminescence (PL) spectra of the organic metal compounds (I)-(IV) of the disclosure.

The following description is of the best-contemplated mode of carrying out the disclosure. This description is made for the purpose of illustrating the general principles of the disclosure and should not be taken in a limiting sense. The scope of the disclosure is best determined by reference to the appended claims.

Organic Metal Compound

According to an embodiment of the disclosure, the disclosure provides an organic metal compound having Formula (I):

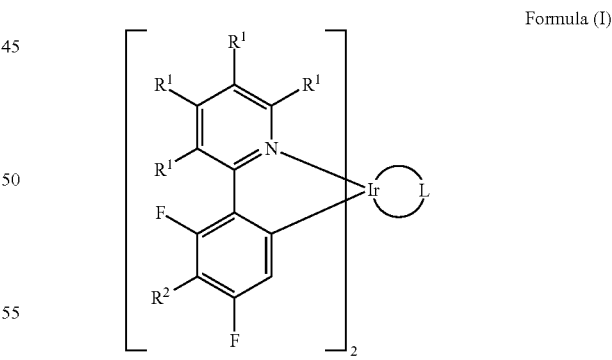

Formula (I)

wherein, each $R^1$ can be independently hydrogen, halogen, $C_{1-10}$ alkyl group, $C_{5-10}$ cycloalkyl group, or $C_{5-12}$ aryl group; $R^2$ can be trialkyl silyl group; and, L can be picolinic acid ligand, 2-(imidazol-2-yl) pyridine ligand, 2-(4,5-dimethyl-imidazol-2-yl)pyridine ligand, 3-(trifluoromethyl)-5-(pyridine-2-yl)-1,2,4-triazolate ligand, or 3-(isobutyl)-5-(pyridine-2-yl)-1,2,4-triazolate ligand. Herein, the picolinic acid ligand can be an unsubstituted picolinic acid ligand, or a substituted picolinic acid ligand, such as

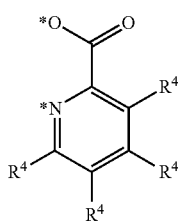

(atoms marked by * are bonded with Ir), wherein each $R^4$ can be independently hydrogen, $C_{1-10}$ alkyl group, $C_{5-10}$ cycloalkyl group, or $C_{5-12}$ aryl group; the 2-(imidazol-2-yl) pyridine ligand can be an unsubstituted 2-(imidazol-2-yl) pyridine ligand, or a substituted 2-(imidazol-2-yl) pyridine ligand, such as

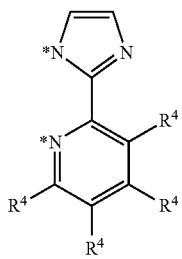

(atoms marked by * are bonded with Ir), wherein each $R^4$ can be independently hydrogen, $C_{1-10}$ alkyl group, $C_{5-10}$ cycloalkyl group, or $C_{5-12}$ aryl group; the 2-(4,5-dimethyl-imidazol-2-yl)pyridine ligand can be an unsubstituted 2-(4, 5-dimethyl-imidazol-2-yl)pyridine ligand, or a substituted 2-(4,5-dimethyl-imidazol-2-yl)pyridine ligand, such as

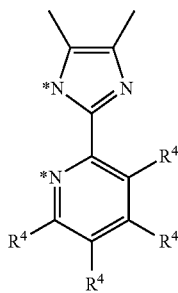

(atoms marked by * are bonded with Ir), wherein each $R^4$ can be independently hydrogen, $C_{1-10}$ alkyl group, $C_{5-10}$ cycloalkyl group, or $C_{5-12}$ aryl group; the 3-(trifluoromethyl)-5-(pyridine-2-yl)-1,2,4-triazolate ligand can be an unsubstituted 3-(trifluoromethyl)-5-(pyridine-2-yl)-1,2,4-triazolate ligand, or a substituted 3-(trifluoromethyl)-5-(pyridine-2-yl)-1,2,4-triazolate ligand, such as

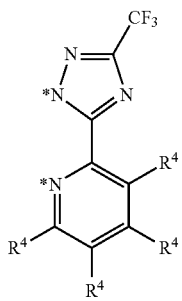

(atoms marked by * are bonded with Ir), wherein each $R^4$ can be independently hydrogen, $C_{1-10}$ alkyl group, $C_{5-10}$ cycloalkyl group, or $C_{5-12}$ aryl group; and, the 3-(isobutyl)-5-(pyridine-2-yl)-1,2,4-triazolate ligand can be an unsubstituted 3-(isobutyl)-5-(pyridine-2-yl)-1,2,4-triazolate ligand, or a substituted 3-(isobutyl)-5-(pyridine-2-yl)-1,2,4-triazolate ligand, such as

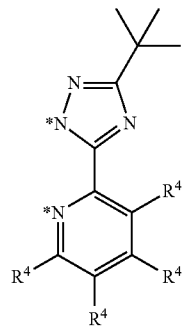

(atoms marked by * are bonded with Ir), wherein each $R^4$ can be independently hydrogen, $C_{1-10}$ alkyl group, $C_{5-10}$ cycloalkyl group, or $C_{5-12}$ aryl group.

According to embodiments of the disclosure, the organic metal compound can serve as a blue phosphorescent dopant material (having a maximum luminous intensity peak of between about 461 nm to 485 nm), and can be applied to an organic light-emitting device for enhancing the luminous efficiency.

According to an embodiment of the disclosure, each $R^1$ can be independently hydrogen, methyl, ethyl, propyl, isopropyl, butyl, isobutyl, tert-butyl, pentyl, hexyl, cyclohexyl, phenyl, biphenyl, or naphthyl; and $R^2$ can be trimethyl silyl group, triethyl silyl group, triphenyl silyl group, tripropyl silyl group, butyldimethyl silyl group, propyldimethyl silyl group, vinyldimethyl silyl group, or t-butyldimethyl silyl group.

According to some embodiments of the disclosure, at least one R1 of the organic metal compound having Formula (I) is not hydrogen.

According to other embodiments of the disclosure, the organic metal compound can be

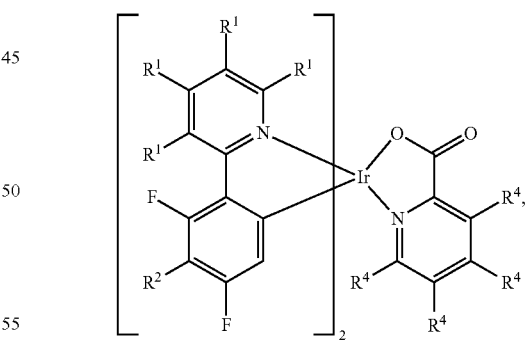

wherein each $R^1$ can be independently hydrogen, halogen, $C_{1-10}$ alkyl group, $C_{5-10}$ cycloalkyl group, or $C_{5-12}$ aryl group; $R^2$ can be trialkyl silyl group; and, each $R^4$ can be independently hydrogen, $C_{1-10}$ alkyl group, $C_{5-10}$ cycloalkyl group, or $C_{5-12}$ aryl group, for example, each $R^1$ can be independently hydrogen, methyl, ethyl, propyl, isopropyl, butyl, isobutyl, tert-butyl, pentyl, hexyl, cyclohexyl, phenyl, biphenyl, or naphthyl; $R^2$ can be trimethyl silyl group, triethyl silyl group, triphenyl silyl group), tripropyl silyl group, butyldimethyl silyl group, propyldimethyl silyl group, vinyldimethyl silyl group, or t-butyldimethyl silyl group; and, each R⁴ can be independently hydrogen, methyl, ethyl, propyl, isopropyl, butyl, isobutyl, tert-butyl, pentyl, hexyl, cyclohexyl, phenyl, biphenyl, or naphthyl.

According to other embodiments of the disclosure, the organic metal compound can be

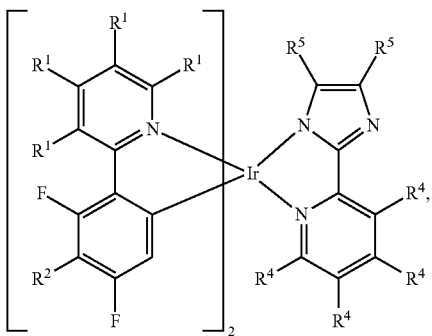

wherein each R¹ can be independently hydrogen, halogen, $C_{1-10}$ alkyl group, $C_{5-10}$ cycloalkyl group, or $C_{5-12}$ aryl group; R² can be trialkyl silyl group; each R⁴ can be independently hydrogen, $C_{1-10}$ alkyl group, $C_{5-10}$ cycloalkyl group, or $C_{5-12}$ aryl group; and, R⁵ is hydrogen, or methyl group, for example, each R¹ can be independently hydrogen, methyl, ethyl, propyl, isopropyl, butyl, isobutyl, tert-butyl, pentyl, hexyl, cyclohexyl, phenyl, biphenyl, or naphthyl; R² can be trimethyl silyl group, triethyl silyl group, triphenyl silyl group, tripropyl silyl group, butyldimethyl silyl group, propyldimethyl silyl group, vinyldimethyl silyl group, or t-butyldimethyl silyl group; and, each R⁴ can be independently hydrogen, methyl, ethyl, propyl, isopropyl, butyl, isobutyl, tert-butyl, pentyl, hexyl, cyclohexyl, phenyl, biphenyl, or naphthyl.

According to other embodiments of the disclosure, the organic metal compound can be

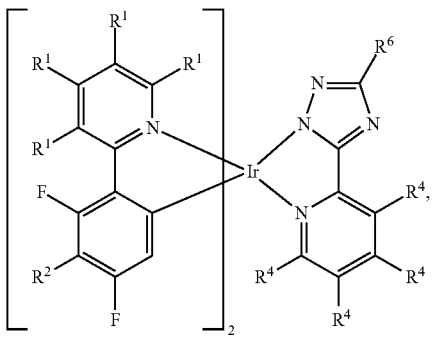

wherein each R¹ can be independently hydrogen, halogen, $C_{1-10}$ alkyl group, $C_{5-10}$ cycloalkyl group, or $C_{5-12}$ aryl group; R² can be trialkyl silyl group; each R⁴ can be independently hydrogen, $C_{1-10}$ alkyl group, $C_{5-10}$ cycloalkyl group, or $C_{5-12}$ aryl group; and, R⁶ can be fluoroalkyl group, tertbutyl group, or isobutyl group. For example, each R¹ can be independently hydrogen, methyl, ethyl, propyl, isopropyl, butyl, isobutyl, tert-butyl, pentyl, hexyl, cyclohexyl, phenyl, biphenyl, or naphthyl; R² can be trimethyl silyl group, triethyl silyl group, triphenyl silyl group, tripropyl silyl group, butyldimethyl silyl group, propyldimethyl silyl group, vinyldimethyl silyl group, or t-butyldimethyl silyl group; and, each R⁴ can be independently hydrogen, methyl, ethyl, propyl, isopropyl, butyl, isobutyl, tert-butyl, pentyl, hexyl, cyclohexyl, phenyl, biphenyl, or naphthyl.

Since there are two fluorine atoms bonded to the benzene ring of the ligand L in the meta-position, a trialkyl silyl group is bonded to the benzene ring of the ligand L between the two fluorine atoms, and the trialkyl silyl group is bonded to the benzene ring of the ligand L via a sp³ carbon-carbon bond, the trialkyl silyl group can prevent the fluorine atoms of the organic metal compound having Formula (I) of the disclosure from being removed from the benzene ring by being attacked from negatively charged particles.

As a result, the organic metal compound having Formula (I) of the disclosure can have great thermal stability and be suitable for being purified by a sublimation process (the organic metal compound having Formula (I) of the disclosure has a sublimation yield that is greater than 80%). In addition, the organic metal compound having Formula (I) of the disclosure, which has a suitable highest occupied molecular orbital (HOMO) and lowest unoccupied molecular orbital (LUMO) energy gap (between 6.0 eV and 3.0 eV), facilitates the electrons recombining with the holes to form excitons, results in luminescence. Therefore, the organic metal compound having Formula (I) of the disclosure can serve as phosphorescent light-emitting material for enhancing the luminous efficiency of the organic light-emitting device employing the same.

According to embodiments of the disclosure, the organic metal compound having Formula (I) of the disclosure can be,

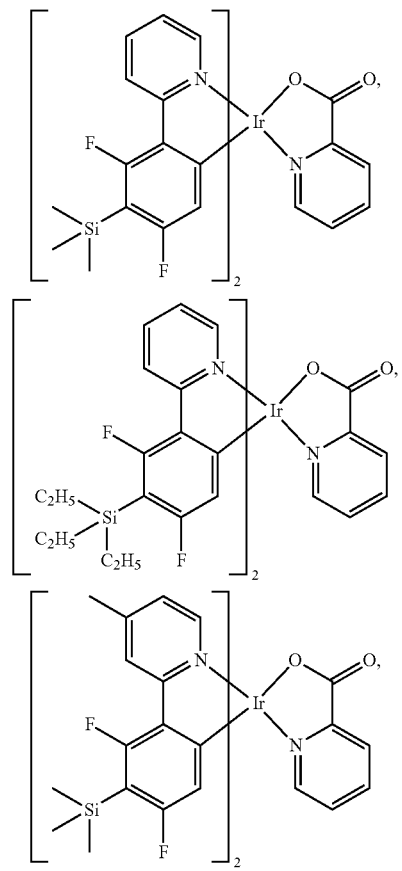

-continued
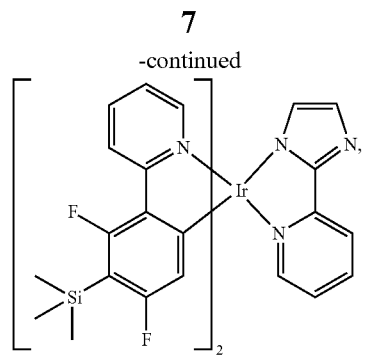
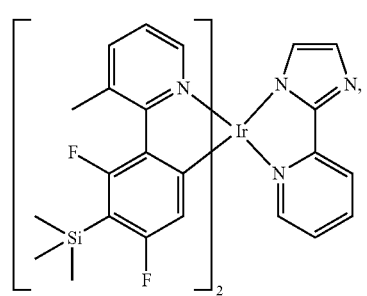
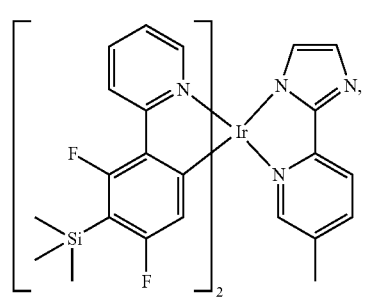
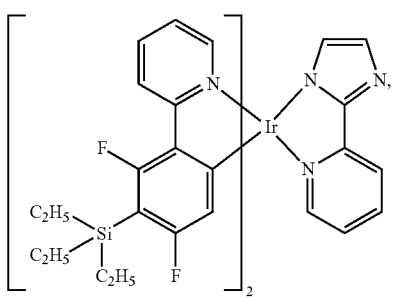
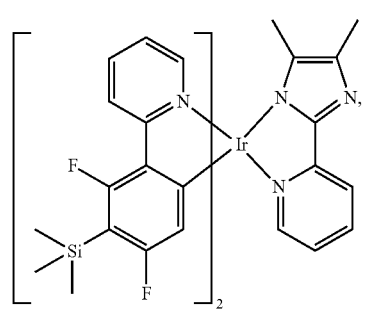
-continued
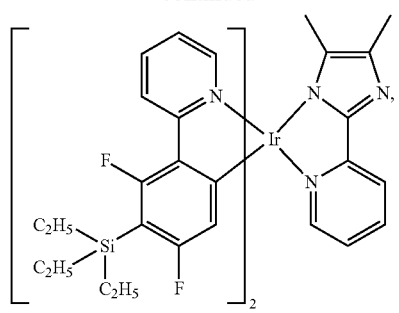
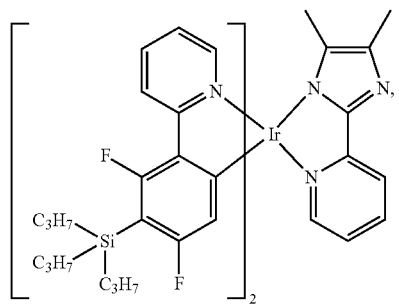
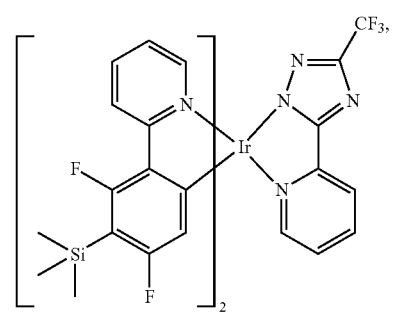
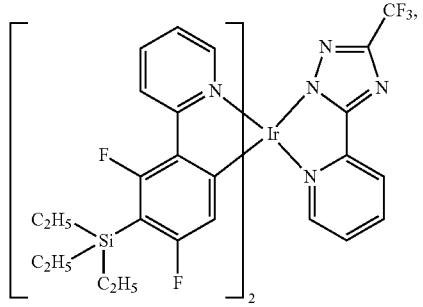
, or -continued

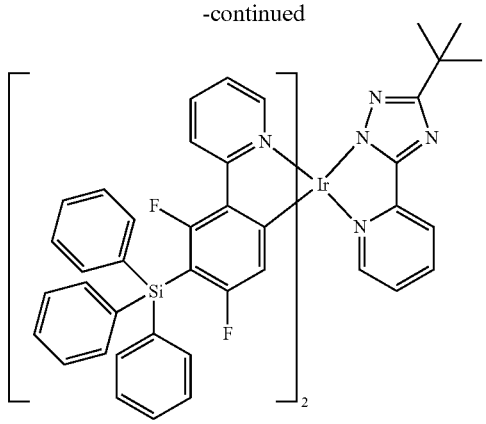

The following examples are intended to illustrate the disclosure more fully without limiting the scope, since numerous modifications and variations will be apparent to those skilled in this art.

Example 1: Preparation of Organic Metal Compound (I)

Organic metal compound (I)

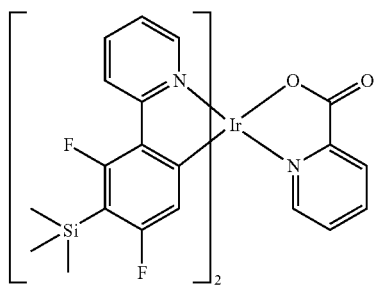

2-bromopyridine (4.5 g, 28.48 mmol), 2,4-difluorophenyl boronic acid (5 g, 31.33 mmol), and $K_2CO_3$ (4.32 g, 31.33 mmol) were added into a 500 mL reaction bottle. Next, dimethoxyethane (180 ml), water (90 ml), and a catalyst amount of tetrakis(triphenylphosphine)palladium (Pd (PPh$_3$)$_4$) were added into the reaction bottle. After removing moisture and purging nitrogen gas several times, the mixture was heated to reflux. After reacting for 8 hr and then cooling to room temperature, NaHCO$_3$ (aq) was added into the reaction bottle to adjust the pH value to a weak base condition. Next, the result was extracted three times using ethyl acetate (EA) and water as the extraction solvent. Next, an organic phase was separated and dried, and then purified by column chromatography, obtaining compound (1). The synthesis pathway of the above reaction was as follows:

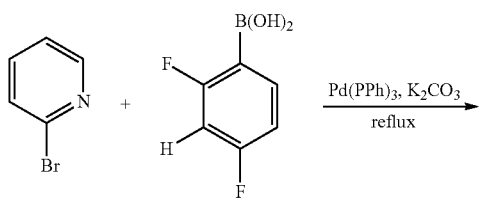

-continued

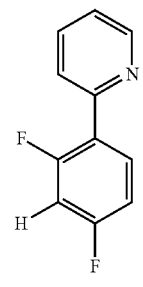

Compound (1)

The physical measurement of the compound (1) is listed below: $^1$H NMR (200 MHz, CDCl$_3$, 294 K): δ 8.71 (d, 1H), 8.00 (q, 1H), 7.77~7.74 (m, 2H), 7.26 (q, 1H), 7.06~6.86 (m, 2H).

Next, compound (1) (2-(4,6-difluorophenyl)pyridine, 5 g (26.17 mmol), and tetrahydrofuran (100 mL) were added into a reaction bottle. After removing moisture and purging nitrogen gas several times, the reaction bottle was cooled down to −78° C., and lithium diisopropylamide (LDA, [(CH$_3$)$_2$CH]$_2$NLi) (15.6 mL, 31.32 mmol was added dropwise into the reaction bottle at −78° C. and then stirred for 1 hr. Next, trimethylsilyl chloride (TMSCl) (4 mL, 31.32 mmol) was added into the reaction bottle at 0° C. Next, the result was extracted three times using ethyl acetate (EA) and water as the extraction solvent. Next, an organic phase was separated and dried, and then purified by column chromatography, obtaining compound (2) with a yield of 75%. The synthesis pathway of the above reaction was as follows:

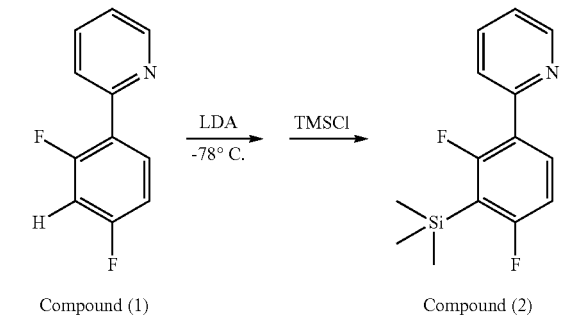 [SMILES: "TMSCl" ; Fc1ccc(-c2ccccn2)c(F)c1 ; C[Si](C)(C)c1c(F)ccc(-c2ccccn2)c1F]

The physical measurement of the compound (2) is listed below: $^1$H NMR (200 MHz, CDCl$_3$, 294 K): δ 8.71 (d, 1H), 7.92 (q, 1H), 7.76~7.73 (m, 2H), 7.25 (t, 1H), 6.84 (t, 1H). Elemental analysis: $C_{14}H_{15}F_2$NSi: N, 5.32, C, 63.85, H, 5.74; Found: N, 5.34, C, 63.75, H, 5.71.

Next, compound (2) (1 g, 3.8 mmol), IrCl$_3$ (0.51 g, 1.7 mmol), and triethylamine (Et$_3$N) (0.53 ml, 3.8 mmol) were added into the reaction bottle. Next, dimethoxyethane (15 mL) was water (5 ml) added into the reaction bottle. After removing moisture and purging nitrogen gas several times, the reaction bottle was heated to 120° C. for 8 hr. After cooling down to room temperature, the result was filtrated. The filter cake was collected and washed with water and hexane, and then dried under vacuum, obtaining compound (3). The synthesis pathway of the above reaction was as follows:

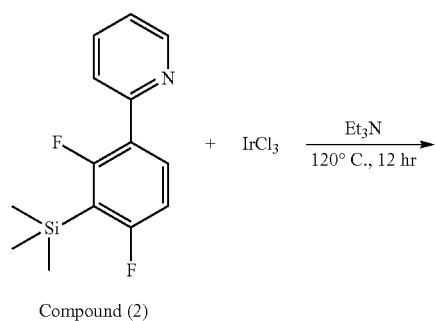

Compound (2)

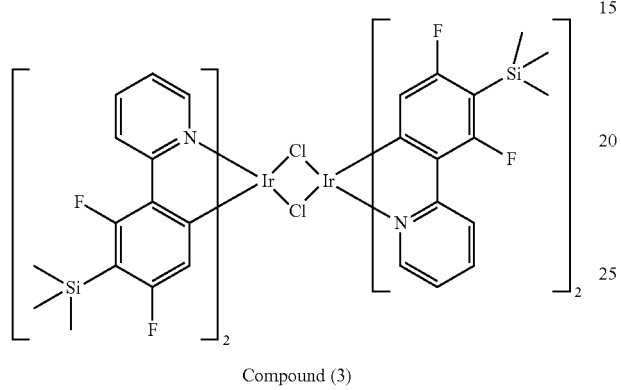

Compound (3)

The physical measurement of the compound (3) is listed below: $^1$H NMR (200 MHz, CDCl$_3$, 294 K): δ 9.09 (d, 4H), 8.31 (d, 4H), 7.79 (t, 4H), 6.78 (t, 4H), 5.28 (d, 4H), 0.23 (s, 36H).

Next, compound (3) (0.5 g, 0.33 mmol), picolinic acid (164 mg, 1.33 mmol), and triethylamine (Et$_3$N) (0.1 ml 1.33 mmol) were added into a reaction bottle. Next, dimethoxyethane (5 mL) was added into the reaction bottle. After removing moisture and purging nitrogen gas several times, the reaction bottle was heated to 120° C. for 3 hr. After cooling down to room temperature, the result was filtrated. The filter cake was collected and washed with water and hexane, and then dissolved into CH$_2$Cl$_2$. The result was extracted three times by CH$_2$Cl$_2$ and water as the extraction solvent. Next, an organic phase was separated and dried. Finally, the result was purified by a sublimation process, obtaining organic metal compound (I) with a yield that was greater than 80%. The synthesis pathway of the above reaction was as follows:

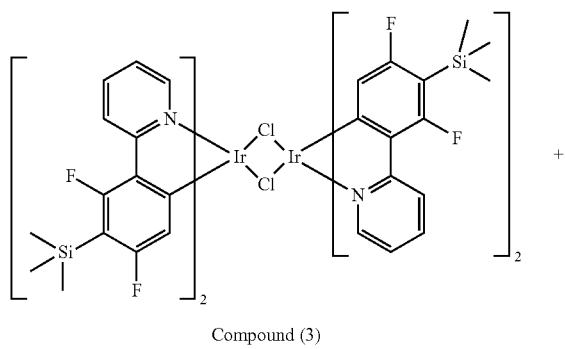

Compound (3)

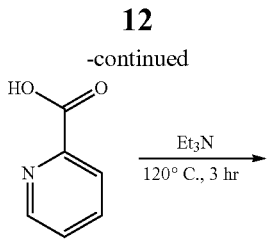

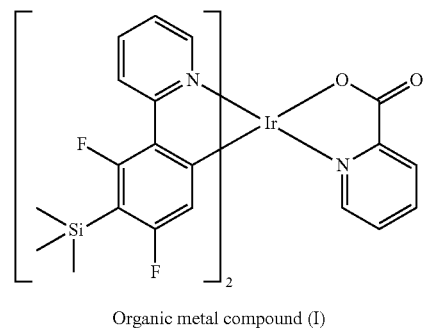

Organic metal compound (I)

The physical measurement of the organic metal compound (I) is listed below: $^1$H NMR (200 MHz, CDCl$_3$, 294 K): δ 8.73 (d, 1H), 8.34~8.22 (m, 3H), 7.94 (dt, 1H), 7.80~7.71 (m, 3H), 7.47~7.40 (m, 2H), 7.15 (t, 1H), 6.93 (t, 1H), 5.80 (d, 1H), 5.54 (d, 1H), 0.34 (s, 9H), 0.29 (s, 9H). Elemental analysis: C$_{34}$H$_{32}$F$_4$IrN$_3$O$_2$Si$_2$: N, 5.01, C, 48.67, H, 3.84; Found: N, 4.99, C, 48.72, H, 3.88.

Example 2: Preparation of Organic Metal Compound (II)

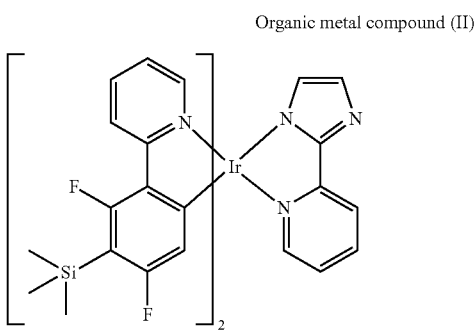

Organic metal compound (II)

Next, compound (3) (0.5 g, 0.33 mmol), 2-(1H-imidazol-2-yl)pyridine (193 mg, 1.33 mmol), and triethylamine (Et$_3$N) (0.1 ml, 1.33 mmol) were added into a reaction bottle. Next, dimethoxyethane (5 mL) was added into the reaction bottle. After removing moisture and purging nitrogen gas several times, the reaction bottle was heated to 120° C. for 3 hr. After cooling down to room temperature, the result was filtrated. The filter cake was collected and washed with water and hexane, and then dissolved into CH$_2$Cl$_2$. The result was extracted three times by CH$_2$Cl$_2$ and water as the extraction solvent. Next, an organic phase was separated and dried by a rotavapor. Finally, the result was purified by a sublimation process, obtaining organic metal compound (II) with a yield that was greater than 80%. The synthesis pathway of the above reaction was as follows:

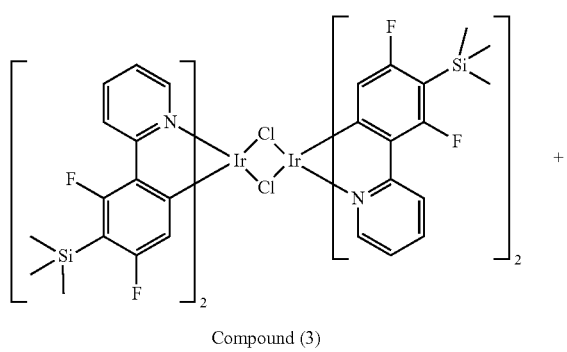

Compound (3)

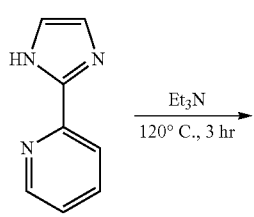

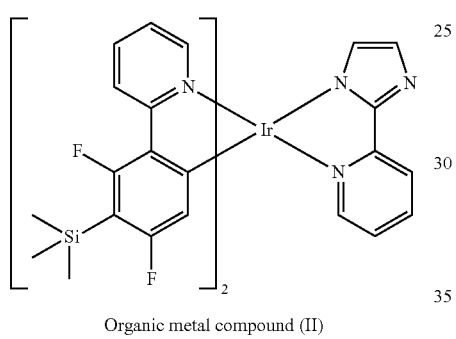

Organic metal compound (II)

The physical measurement of the organic metal compound (II) is listed below: $^1$H NMR (200 MHz, CDCl$_3$, 294 K): δ 8.25 (d, 2H), 7.82~7.60 (m, 7H), 7.28 (s, 1H), 7.04 (t, 1H), 6.91 (q, 2H), 6.57 (s, 1H), 5.82 (d, 1H), 5.69 (d, 1H), 0.34 (s, 18H). Elemental analysis: C$_{36}$H$_{34}$F$_4$IrN$_5$Si$_2$: N, 8.13, C, 50.21, H, 3.98; Found: N, 8.10, C, 50.17, H, 4.03.

Example 3: Preparation of Organic Metal Compound (III)

Organic metal compound (III)

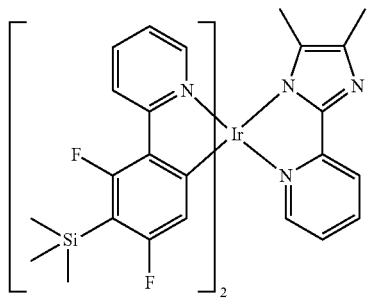

Next, compound (3) (0.5 g, 0.33 mmol), 2-(4,5-dimethyl-1H-imidazol-2-yl)pyridine (230 mg, 1.33 mmol), and triethylamine (Et$_3$N) (0.1 ml, 1.33 mmol) were added into a reaction bottle. Next, dimethoxyethane (5 mL) was added into the reaction bottle. After removing moisture and purging nitrogen gas several times, the reaction bottle was heated to 120° C. for 3 hr. After cooling down to room temperature, the result was filtrated. The filter cake was collected and washed with water and hexane, and then dissolved into CH$_2$Cl$_2$. The result was extracted three times by CH$_2$Cl$_2$ and water as the extraction solvent. Next, an organic phase was separated and dried by a rotavapor. Finally, the result was purified by a sublimation process, obtaining organic metal compound (III) with a yield that was greater than 80%. The synthesis pathway of the above reaction was as follows:

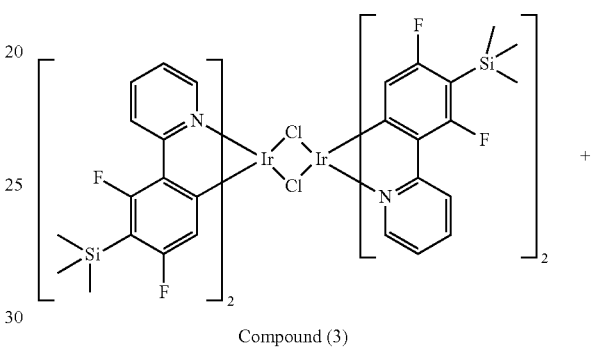

Compound (3)

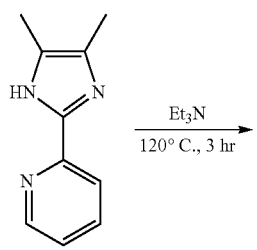

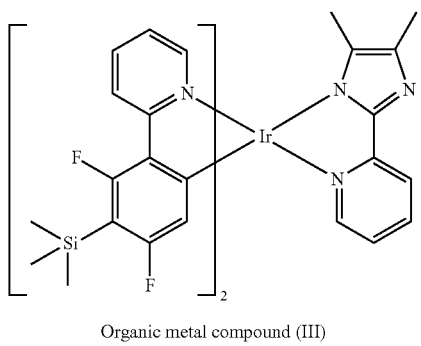

Organic metal compound (III)

The physical measurement of the organic metal compound (III) is listed below: $^1$H NMR (200 MHz, CDCl$_3$, 294 K): δ 8.25~8.23 (m, 3H), 7.79 (d, 1H), 7.73~7.59 (m, 4H), 7.48 (d, 1H), 7.0~6.84 (m, 3H), 5.69 (t, 2H), 2.21 (s, 3H), 1.44 (s, 3H), 0.34 (s, 9H), 0.32 (s, 9H). Elemental analysis: C$_{38}$H$_{38}$F$_4$IrN$_5$Si$_2$: N, 7.88, C, 51.33, H, 4.31; Found: N, 7.93, C, 51.34, H, 4.33.

Example 4: Preparation of Organic Metal Compound (IV)

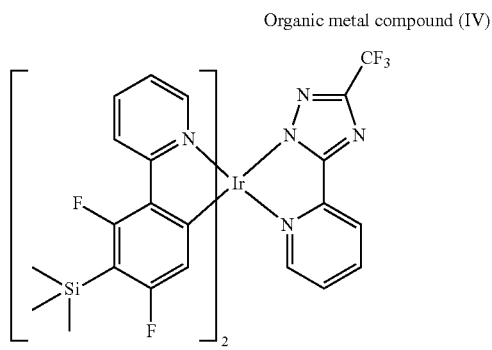

Organic metal compound (IV)

Next, compound (3) (0.5 g, 0.33 mmol), 2-[3-(trifluoromethyl)-1H-1,2,4-triazol-5-yl]pyridine (285 mg, 1.33 mmol), and triethylamine (Et$_3$N) (0.1 ml, 1.33 mmol) were added into a reaction bottle. Next, dimethoxyethane (5 mL) was added into the reaction bottle. After removing moisture and purging nitrogen gas several times, the reaction bottle was heated to 120° C. for 3 hr. After cooling down to room temperature, the result was filtrated. The filter cake was collected and washed with water and hexane, and then dissolved into CH$_2$Cl$_2$. The result was extracted three times by CH$_2$Cl$_2$ and water as the extraction solvent. Next, an organic phase was separated and dried by a rotavapor. Finally, the result was purified by a sublimation process, obtaining organic metal compound (IV) with a yield that was greater than 80%. The synthesis pathway of the above reaction was as follows:

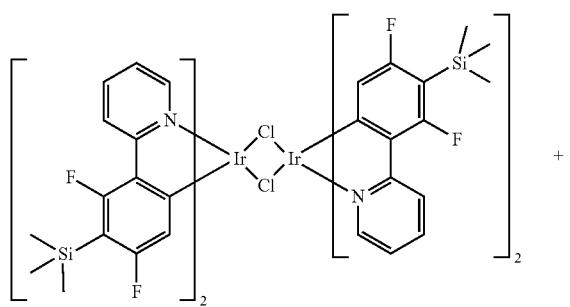

Compound (3)

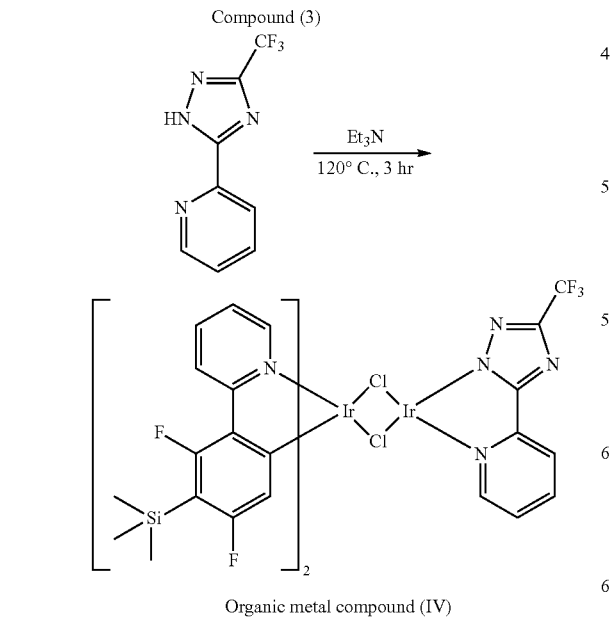

Organic metal compound (IV)

The physical measurement of the organic metal compound (IV) is listed below: $^1$H NMR (200 MHz, CDCl$_3$, 294 K): δ 8.36~8.22 (m, 3H), 7.91 (t, 1H), 7.75~7.66 (m, 4H), 7.40 (d, 1H), 7.27 (t, 1H), 6.97 (t, 1H), 6.86 (t, 1H), 5.73 (d, 1H), 5.64 (d, 1H), 0.35 (s, 9H), 0.32 (s, 9H). Elemental analysis: C$_{36}$H$_{32}$F$_7$IrN$_6$Si$_2$: N, 9.04, C, 46.49, H, 3.47; Found: N, 9.06, C, 46.52, H, 3.45.

Example 5: Preparation of Organic Metal Compound (V)

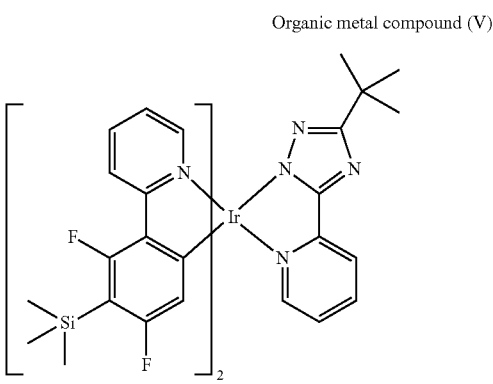

Organic metal compound (V)

Next, compound (3) (0.5 g, 0.33 mmol), 2-[3-(isobutyl)-1H-1,2,4-triazol-5-yl]pyridine (269 mg, 1.33 mmol), and triethylamine (Et$_3$N) (0.1 ml, 1.33 mmol) were added into a reaction bottle. Next, dimethoxyethane (5 mL) was added into the reaction bottle. After removing moisture and purging nitrogen gas several times, the reaction bottle was heated to 120° C. for 3 hr. After cooling down to room temperature, the result was filtrated. The filter cake was collected and washed with water and hexane, and then dissolved into CH$_2$Cl$_2$. The result was extracted three times by CH$_2$Cl$_2$ and water as the extraction solvent. Next, an organic phase was separated and dried by a rotavapor. Finally, the result was purified by a sublimation process, obtaining organic metal compound (V) with a yield that was greater than 80%. The synthesis pathway of the above reaction was as follows:

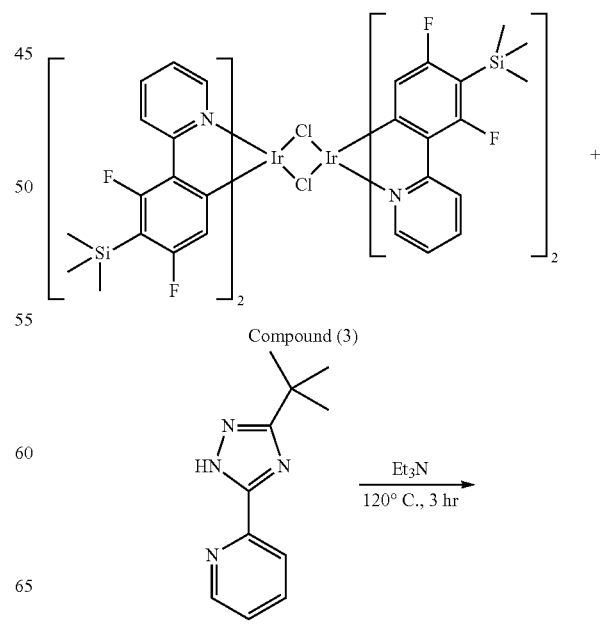

Compound (3)

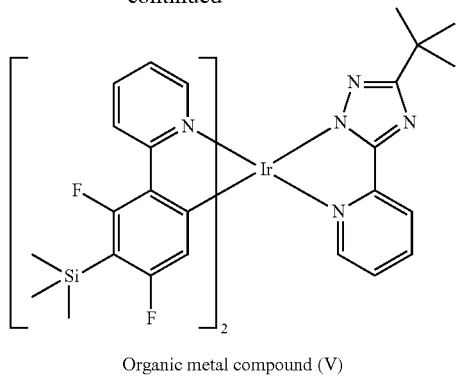

Organic metal compound (V)

The physical measurement of the organic metal compound (V) is listed below: $^1$H NMR (200 MHz, CDCl$_3$, 294 K): δ 8.30~8.18 (m, 3H), 7.80 (t, 1H), 7.69~7.65 (m, 4H), 7.45 (d, 1H), 7.11 (t, 1H), 6.93 (t, 1H), 6.83 (t, 1H), 5.69 (dd, 2H), 1.37 (s, 9H), 0.35 (s, 9H), 0.32 (s, 9H). Elemental analysis: C$_{39}$H$_{41}$F$_4$IrN$_6$Si$_2$: N, 9.15, C, 51.02, H, 4.50; Found: N, 9.18, C, 51.00, H, 4.54.

As shown in Example 1, compound (2) (2-(3-trimethylsilyl-2,4-difluorophenyl)pyridine) can further react with Ir to form the ligand of the disclosure. The preparation of compound (2) (2-(3-trimethylsilyl-2,4-difluorophenyl)pyridine) is easy (prepared via two steps) and the yield of the compound (2) is high (≥70% yield the two steps).

The conventional phosphorescent material FIr(pic) (having a structure represented by

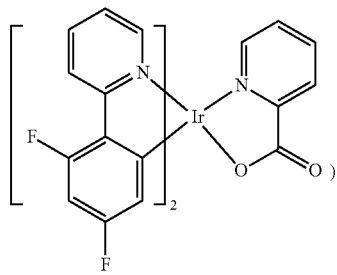

has a sublimation yield of about 50%. On the other hand, since there are two fluorine atoms bonded to the benzene ring of the ligand L in the meta-position, a trialkyl silyl group is bonded to the benzene ring of the ligand L between the two fluorine atoms, and the trialkyl silyl group is bonded to the benzene ring of the ligand L via a sp$^3$ carbon-carbon bond, the trialkyl silyl group can prevent the fluorine atoms of the organic metal compound having Formula (I) of the disclosure from being removed from the benzene ring by being attacked from negatively charged particles. Therefore, the organic metal compound having Formula (I) of the disclosure is suitable for being purified by a sublimation process (i.e. the organic metal compound having Formula (I) of the disclosure has a sublimation yield that is greater than 80%).

Next, the organic metal compounds (I)-(II) and (IV) were dissolved into CH$_2$Cl$_2$ respectively obtaining solutions with a concentration of 10$^{-5}$ M. Next, the photoluminescence (PL) spectra and the maximum luminous intensity peak (Emission λmax) of the solutions were measured, and the results are shown in FIG. 1 and Table 1.

TABLE 1

| | maximum luminous intensity peak (Emission λmax) |
|---|---|
| organic metal compound (I) | 470 nm |
| organic metal compound (II) | 466 nm |
| organic metal compound (IV) | 461 nm |

As shown in FIG. 1 and Table 1, the organic metal compounds of the disclosure having a strong electron-withdrawing ligand (such as: picolinic acid ligand, 2-(1H-imidazol-2-yl) pyridine ligand, or 3-(trifluoromethyl)-5-(pyridine-2-yl)-1,2,4-triazolate ligand) can exhibit a blue-shifted emission and serve as blue phosphorescent material. For example, the maximum luminous intensity peak (461 nm) of the organic metal compound (IV) can have a 14 nm blue-shift in comparison with the maximum luminous intensity peak (475 nm) of the conventional phosphorescent material FIr(pic).

Organic Light-Emitting Device

Figure 2:
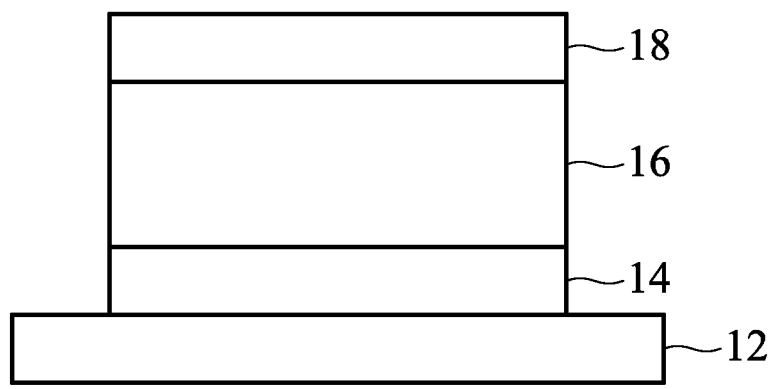
FIG. 2 shows a cross section of an organic light-emitting device disclosed by an embodiment of the disclosure.

FIG. 2 shows an embodiment of an organic light-emitting device 10. The organic light-emitting device 10 includes a substrate 12, a bottom electrode 14, an organic light-emitting element 16, and a top electrode 18, as shown in FIG. 2. The organic light-emitting device can be a top-emission, bottom-emission, or dual-emission devices. The substrate 12 can be a glass, plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Furthermore, at least one of the bottom and top electrodes 14 and 18 is transparent.

The organic light-emitting element 16 at least includes an emission layer, and can further include a hole injection layer, a hole transport layer, an electron transport layer, and an electron injection layer. In an embodiment of the disclosure, at least one layer of the organic light-emitting element 16 includes the aforementioned organometallic compound.

According to another embodiment of the disclosure, the organic light-emitting device can be a phosphorescent organic light-emitting device, and the emission layer of the organic light-emitting element can include a host material and a dopant, wherein the dopant can include the aforementioned organic compounds. The dose of the dopant is not limited and can be optionally modified by a person of ordinary skill in the field.

In order to clearly disclose the organic light-emitting devices of the disclosure, the following examples (having an emitting layer employing the organic metal compounds of the disclosure formed by deposition (dry process) or coating (wet process)) are intended to illustrate the disclosure more fully without limiting their scope, since numerous modifications and variations will be apparent to those skilled in this art.

Example 6: Organic Light-Emitting Device (I)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, TAPC (1,1-bis[4-[N,N'-di(p-tolyl)amino]phenyl] cyclohexane, with a thickness of 40 nm), 26DCzPPy (having a structure represented by

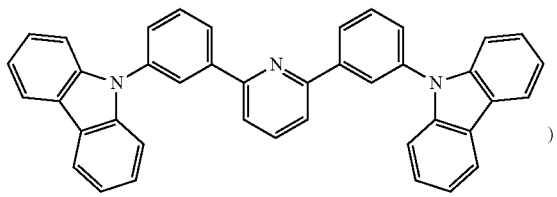 [SMILES: c1cc(-c2cccc(-c3cccc(-n4c5ccccc5c5ccccc54)c3)n2)cc(-n2c3ccccc3c3ccccc32)c1]

)

doped with the organic metal compound (IV) of Example 5 (the weight ratio between 26DCzPPy and the organic metal compound (IV) was 100:15, with a thickness of 10 nm). TmPyPB (1,3,5-tri(p-pyrid-3-yl-phenyl)benzene, with a thickness of 50 nm), LiF (with a thickness of 0.5 nm), and Al (with a thickness of 120 nm) were subsequently formed on the ITO film at $10^6$ torr, obtaining the organic light-emitting device (I) after encapsulation. The materials and layers formed therefrom are described in the following: ITO/TAPC/26DCzPPy: organic metal compound (IV) (15%)/TmPyPB/LiF/Al Next, the optical properties of the light-emitting device (I) were measured by a spectra colorimeter PR650 (purchased from Photo Research Inc.) and a luminance meter LS110 (purchased from Konica Minolta). The results are shown in Table 2.

Example 7: Organic Light-Emitting Device (II)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT(poly(3,4)-ethylendioxythiophen):PSS(e-polystyrenesulfonate) was coated on the ITO film by a blade and spin coating process (with a rotation rate of 4000 rpm) and baked at 100° C. for 40 min to form a PEDO:PSS film serving as a hole injection layer (with a thickness of 50 nm). Next, a composition used for forming a light-emitting layer coated on the PEDO:PSS film by a blade coating process and baked at 100° C. for 40 min to form the light-emitting layer (with a thickness of 30 nm). The composition used for forming a light-emitting layer includes mCP (N,N'-dicarbazolyl-3,5-dibenzene) and the organic metal compound (IV) of Example 5, wherein the weight ratio of mCP and the organic metal compound (IV) was 90:10, dissolved in chlorobenzene. Next, TmPyPB (1,3,5-tri(p-pyrid-3-yl-phenyl) benzene was coated on the light-emitting layer by a spin coating process to form a TmPyPB film (with a thickness of 45 nm). Next, LiF (with a thickness of 1 nm), and Al (with a thickness of 100 nm) were subsequently formed on the TmPyPB film at 10-6 Pa, obtaining the organic light-emitting device (II) after encapsulation. The materials and layers formed therefrom are described in the following: ITO/PEDOT/mCP: organic metal compound (IV)/TmPyPB/LiF/Al.

Next, the optical properties of the light-emitting device (II) were measured by a spectra colorimeter PR650 (purchased from Photo Research Inc.) and a luminance meter LS110 (purchased from Konica Minolta). The results are shown in Table 2.

TABLE 2

| | current efficiency (Cd/A) | power efficiency (lm/W) | maximum luminous intensity peak (nm) | C.I.E COORDINATE |
|---|---|---|---|---|
| organic light-emitting device (I) | 19.2 | 11.0 | 464 | (0.15, 0.26) |
| organic light-emitting device (II) | 11.1 | 7.0 | 460 | (0.16, 0.27) |

Comparative Example 1: Organic Light-Emitting Device (III)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, TAPC (1,1-bis[4-[N,N'-di(p-tolyl)amino]phenyl] cyclohexane, with a thickness of 40 nm), TCTA (4,4',4'-tri (N-carbazolyl)triphenylamine) doped with FIr(pic) (the weight ratio between TCTA and FIr(pic) was 100:6, with a thickness of 10 nm), CzDBS (having a structure represented by

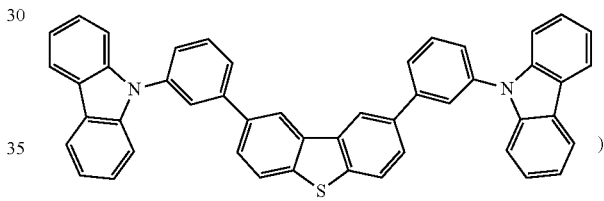

)

doped with FIr(pic) (The ratio between CzDBS and FIr(pic) was 100:6, with a thickness of 10 nm), TmPyPB (1,3,5-tri (p-pyrid-3-yl-phenyl)benzene, with a thickness of 40 nm), LiF (with a thickness of 0.5 nm), and Al (with a thickness of 120 nm), were subsequently formed on the light-emitting layer at $10^{-6}$ torr, obtaining the organic light-emitting device (II) after encapsulation. The materials and layers formed therefrom are described in the following: ITO/TAPC/TCTA: FIr(pic) (6%)/CzDBS: FIr(pic) (6%)/TmPyPB/LiF/Al Next, the optical properties of the light-emitting device (III) were measured by a spectra colorimeter PR650 (purchased from Photo Research Inc.) and a luminance meter LS110 (purchased from Konica Minolta). The light-emitting device (III) has a current efficiency of 37.6 Cd/A, a power efficiency of 25.1 lm/W, a maximum luminous intensity peak of 475 nm, and a C.I.E coordinate of 0.18, 0.38.

During the formation of the light-emitting device (II) via a wet process, it shows that the organic metal compound (IV) exhibit high solubility when the solvent has a solid content that is more than 4 wt %. Therefore, the organic metal compound of the disclosure can be uniformly mixed with the TCTA or mCP.

Figure 3:
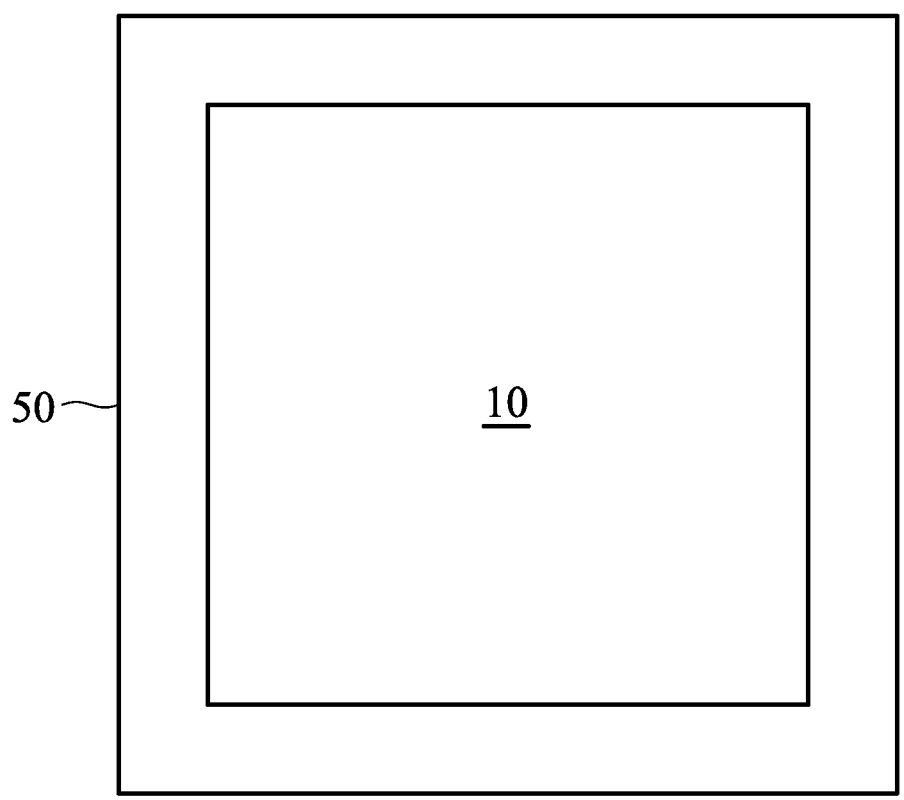
FIG. 3 schematically shows a block diagram of a lighting device according to an embodiment of the disclosure.

FIG. 3 schematically shows a block diagram of a lighting device 100 according to an embodiment of the disclosure. For example, the lighting device 100 can be indoor lighting, a street lamp, car lighting, or a backlight source of a display device. The lighting device 100 of the disclosure can include the aforementioned organic light-emitting device 10 and a lead frame 50. In particular, the organic light-emitting device 10 is fixed on the lead frame 50, and the organic light-emitting device 10 connects to a power source via the lead frame 50.

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic metal compound, having a Formula (I):

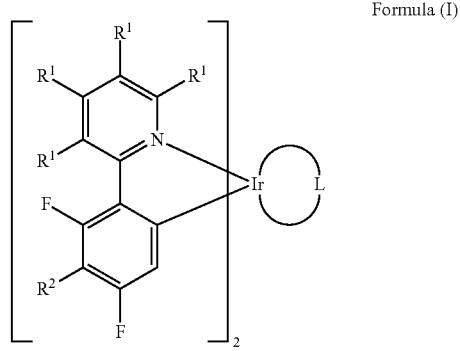

Formula (I)

wherein, each $R^1$ is hydrogen; $R^2$ is trialkyl silyl group; and, L is picolinic acid ligand, 2-(imidazol-2-yl) pyridine ligand, 2-(4,5-dimethyl-imidazol-2-yl)pyridine ligand, 3-(trifluoromethyl)-5-(pyridine-2-yl)-1,2,4-triazolate ligand, or 3-(isobutyl)-5-(pyridine-2-yl)-1,2,4-triazolate ligand, and wherein the organic metal compound has a maximum luminous intensity peak of between 461 nm to 485 nm.

2. The organic metal compound as claimed in claim 1, wherein $R^2$ is trimethyl silyl group, triethyl silyl group, triphenyl silyl group, tripropyl silyl group, butyl dimethyl silyl group, propyl dimethyl silyl group, vinyl dimethyl silyl group, or isobutyl dimethyl silyl group.

3. The organic metal compound as claimed in claim 1, wherein the organic metal compound is

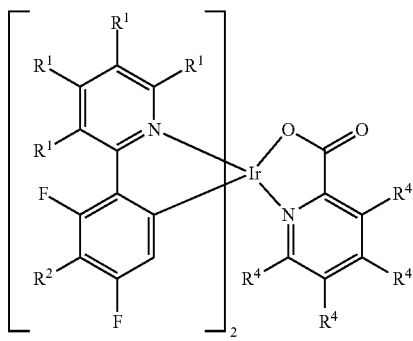

wherein, each $R^1$ is hydrogen; $R^2$ is trialkyl silyl group; and, each $R^4$ is independently hydrogen, $C_{1-10}$ alkyl group, $C_{5-10}$ cycloalkyl group, or $C_{5-12}$ aryl group.

4. The organic metal compound as claimed in claim 3, wherein $R^2$ is trimethyl silyl group, triethyl silyl group, triphenyl silyl group, tripropyl silyl group, butyl dimethyl silyl group, propyl dimethyl silyl group, vinyl dimethyl silyl group, or isobutyl dimethyl silyl group.

5. The organic metal compound as claimed in claim 3, wherein each $R^4$ is independently hydrogen, methyl group, ethyl group, propyl group, isopropyl group, butyl group, isobutyl group, tert-butyl group, pentyl group, hexyl group, cyclohexyl group, phenyl group, biphenyl group, or naphthyl group.

6. The organic metal compound as claimed in claim 1, wherein the organic metal compound is

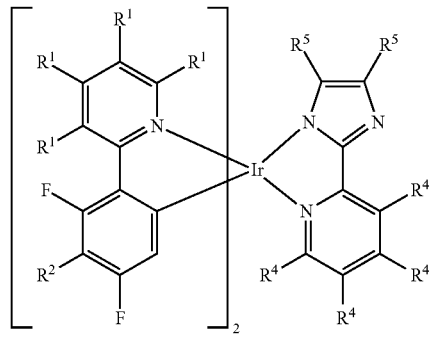

wherein, each $R^1$ is hydrogen; $R^2$ is trialkyl silyl group; each $R^4$ is independently hydrogen, $C_{1-10}$ alkyl group, $C_{5-10}$ cycloalkyl group, or $C_{5-12}$ aryl group; and, $R^5$ is hydrogen, or methyl group.

7. The organic metal compound as claimed in claim 6, wherein $R^2$ is trimethyl silyl group, triethyl silyl group, triphenyl silyl group, tripropyl silyl group, butyl dimethyl silyl group, propyl dimethyl silyl group, vinyl dimethyl silyl group, or isobutyl dimethyl silyl group.

8. The organic metal compound as claimed in claim 6, wherein each $R^4$ is independently hydrogen, methyl group, ethyl group, propyl group, isopropyl group, butyl group, isobutyl group, tert-butyl group, pentyl group, hexyl group, cyclohexyl group, phenyl group, biphenyl group, or naphthyl group.

9. The organic metal compound as claimed in claim 1, wherein the organic metal compound is

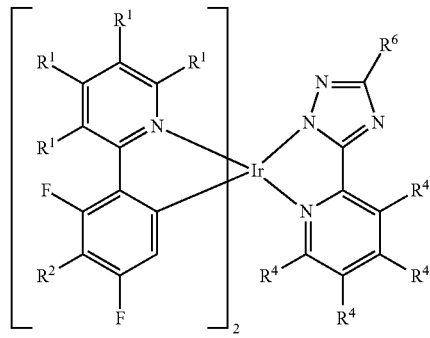

wherein, each $R^1$ is hydrogen; $R^2$ is trialkyl silyl group; each $R^4$ is independently hydrogen, $C_{1-10}$ alkyl group, $C_{5-10}$ cycloalkyl group, or $C_{5-12}$ aryl group; and, $R^6$ is fluoromethyl group, or isobutyl group.

10. The organic metal compound as claimed in claim 9, wherein $R^2$ is trimethyl silyl group, triethyl silyl group, triphenyl silyl group, tripropyl silyl group, butyl dimethyl silyl group, propyl dimethyl silyl group, vinyl dimethyl silyl group, or isobutyl dimethyl silyl group.

11. The organic metal compound as claimed in claim 9, wherein each $R^4$ is independently hydrogen, methyl group, ethyl group, propyl group, isopropyl group, butyl group, isobutyl group, tert-butyl group, pentyl group, hexyl group, cyclohexyl group, phenyl group, biphenyl group, or naphthyl group.

12. An organic light-emitting device, comprising:
a pair of electrodes; and,
an organic light-emitting element, disposed between the pair of electrodes, wherein the organic light-emitting element comprises the organic metal compound as claimed in claim 1.

13. A lighting device, comprising:
a lead frame; and
the organic light-emitting device as claimed in claim 12 disposed on the lead frame.

* * * * *